US012753175B2

(12) United States Patent
Chen et al.

(10) Patent No.: US 12,753,175 B2
(45) Date of Patent: Oct. 6, 2026

(54) PROCESS FOR THE PREPARATION OF (9S)-2-BROMO-9-(2,3,4-TRIFLUOROPHENYL)-6,7,8,9-TETRAHYDRO-5H-[1,2,4]TRIAZOLO [1,5-A]AZEPINE

(71) Applicant: Hoffmann-La Roche Inc., Little Falls, NJ (US)

(72) Inventors: Weichun Chen, Shanghai (CN); Christian Jenny, Basel (CH); Hasane Ratni, Habsheim (FR); Guocai Zhang, Shanghai (CN); Fugui Zhang, Jiangsu (CN)

(73) Assignee: Hoffmann-La Roche Inc., Branchburg, NJ (US)

( * ) Notice: Subject to any disclaimer, the term of this patent is extended or adjusted under 35 U.S.C. 154(b) by 708 days.

(21) Appl. No.: 17/780,127

(22) PCT Filed: Nov. 27, 2020

(86) PCT No.: PCT/EP2020/083600

§ 371 (c)(1),
(2) Date: May 26, 2022

(87) PCT Pub. No.: WO2021/105337

PCT Pub. Date: Jun. 3, 2021

(65) Prior Publication Data

US 2023/0048657 A1 Feb. 16, 2023

(51) Int. Cl.

| | |
|---|---|
| ***C07D 487/04*** | (2006.01) |
| ***C07C 51/353*** | (2006.01) |
| ***C07C 51/41*** | (2006.01) |
| ***C07C 51/60*** | (2006.01) |
| ***C07C 57/58*** | (2006.01) |
| ***C07C 213/08*** | (2006.01) |
| ***C07C 215/34*** | (2006.01) |
| ***C07C 277/08*** | (2006.01) |

(52) U.S. Cl.

CPC .......... *C07D 487/04* (2013.01); *C07C 51/353* (2013.01); *C07C 51/412* (2013.01); *C07C 51/60* (2013.01); *C07C 57/58* (2013.01); *C07C 213/08* (2013.01); *C07C 215/34* (2013.01); *C07C 277/08* (2013.01); *C07B 2200/07* (2013.01)

(58) Field of Classification Search

CPC .................................................... C07D 487/04

See application file for complete search history.

(56) References Cited

U.S. PATENT DOCUMENTS 11,370,802 B2 * 6/2022 Ratni .................. C07D 487/04
11,440,915 B2 * 9/2022 Bartels .................. A61P 25/28

FOREIGN PATENT DOCUMENTS

| | | | |
|---|---|---|---|
| JP | S58-29719 | 2/1983 | |
| JP | 2001-139516 | 5/2001 | |
| WO | 2010/083141 A1 | 7/2010 | |
| WO | 2011/086098 A1 | 7/2011 | |
| WO | WO-2018083050 A1 * | 5/2018 | ............. A61P 25/28 |
| WO | 2019/121434 A1 | 6/2019 | |
| WO | 2019141832 A1 | 7/2019 | |
| WO | 2020/120521 A1 | 6/2020 | |
| WO | 2020/136188 A1 | 7/2020 | |

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "ZINC—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/Zregistry (CAS Registrysm) Sep. 2016 2 pages.*
Ratni ACS Medicinal Chemistry Letters, 2020, 11(6), 1257-1268.*
Cahill, Patent Claim Construction of Enantiomers, Tul. J. Tech. & Intell. Prop. [vol. 15, 61-87, 2012.*
International Search Report with Written Opinion—PCT/EP2020/083600 mailed Feb. 18, 2021, pp. 1-10.
International Preliminary Report on Patentability—PCT/EP2020/083600 issued May 17, 2022, pp. 1-7.

* cited by examiner

*Primary Examiner* — Nizal S Chandrakumar
(74) *Attorney, Agent, or Firm* — Genentech, Inc.

(57) ABSTRACT

The present invention relates to a process for synthesizing large scale a compound of formula (I), or pharmaceutically acceptable salt thereof, which is useful as the key intermediate for the synthesis of compounds for prophylaxis and treatment of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

(I)

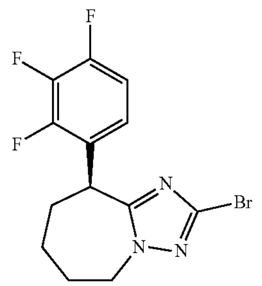

2 Claims, No Drawings

PROCESS FOR THE PREPARATION OF (9S)-2-BROMO-9-(2,3,4-TRIFLUOROPHENYL)-6,7,8,9-TETRAHYDRO-5H-[1,2,4]TRIAZOLO[1,5-A]AZEPINE

CROSS-REFERENCE TO RELATED APPLICATIONS

This application is a National Stage Entry under 35 U.S.C. § 371 of International Application No. PCT/EP2020/083600, filed Nov. 27, 2020, which claims benefit of priority under 35 U.S.C. § 119 (a) to Application No. PCT/CN2019/122086 filed in P.R. China, Nov. 29, 2019, each of which is incorporated herein by reference in its entirety.

The present invention relates to a process for the preparation of a compound (I), (I)

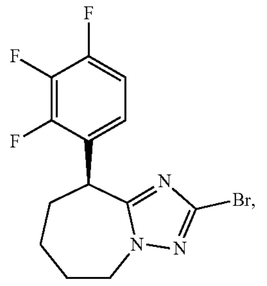

(9S)-2-bromo-9-(2,3,4-trifluorophenyl)-6,7,8,9-tetrahydro-5H-[1,2,4]triazolo[1,5-a]azepine, or pharmaceutically acceptable salt thereof, which is useful as the key intermediate for the synthesis of compounds for prophylaxis and treatment of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

BACKGROUND OF THE INVENTION

The related synthetic approach of compound (I) was disclosed in patents WO2019121434, WO2018083050, WO2011086098 and WO2010083141, however, the current several processes are not suitable for large scale production due to the following issues:

(a) column purification with tedious work up process is needed for step 1 to make 6-chloro-2-(2,3,4-trifluorophenyl) hexanoic acid, compound (III), with lower yield.

(b) chiral separation is needed at the end to get desired chiral product with huge cost concern and process hurdles for large scale production for compound (I).

(c) for the synthesis of key intermediate, amino tri-azole compound (VII), the previous synthetic route from methyl ester of 6-chloro-2-(2,3,4-trifluorophenyl) hexanoic acid as in WO2011086098 can only provide very low yield (~15%) while current process significantly improved the yield to ~50%.

(d) possible racemization and column purification in the later steps synthesis even if chiral centre is generated in the step 6 if published process was used.

(e) safe, robust and scalable concerns for the newly form high energy tri-azole ring during large scale production.

Based on the issues above, one object of this invention therefore is to find an efficient synthetic route and approach, which can address all of above issues and be applied on a large-scale chiral compound (I) production.

Another embodiment of the present invention relates to a novel process for the preparation of a compound (IV) and/or compound (IVa):

IV

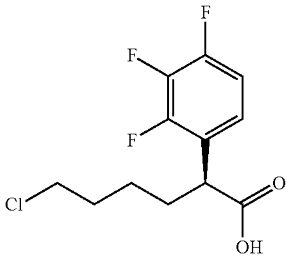

IVa

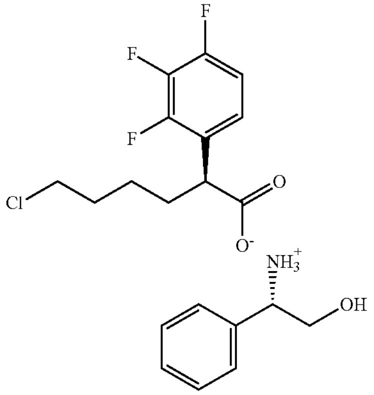

DETAILED DESCRIPTION OF THE INVENTION

Definitions

The term "pharmaceutically acceptable salt" refers to conventional acid-addition salts or base-addition salts that retain the biological effectiveness and properties of the compounds of (I) and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435; or in Ansel, H., et al., In: Pharmaceutical Dosage Forms and Drug Delivery Systems, 6th ed. (1995), pp. 196 and 1456-1457.

Abbreviation aq. Aqueous solution
API Active Pharmaceutical Ingredient
DBU 1,8-Diazabicyclo[5.4.0]undec-7-ene
DCM Dichloromethane
DIPEA N,N-Diisopropylethylamine
eq. Equivalent
EtOAc or EA Ethyl acetate
IPC In process control
IPA Isopropanol
IPAc Isopropyl acetate
ML Mother liquor
2-MeTHF 2-Methyltetrahydrofuran
MTBE Methyl tert-butyl ether
NaHMDS Sodium hexamethyldisilazide in THF
NMP N-Methyl-2-pyrrolidone
Pd/C Palladium on carbon
TEA Triethylamine
v. Volume
v/v Volume ratio
wt. % Weight percentage The present invention provides a process for preparing the compounds of formula (I) as outlined in the scheme 1.

Scheme 1

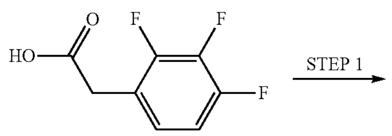

II

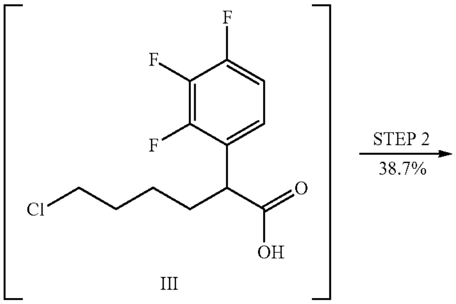

III

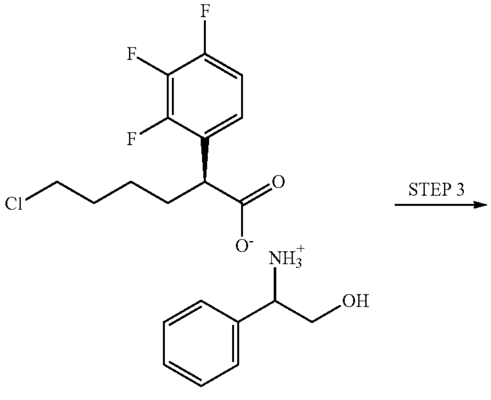

IVa

-continued

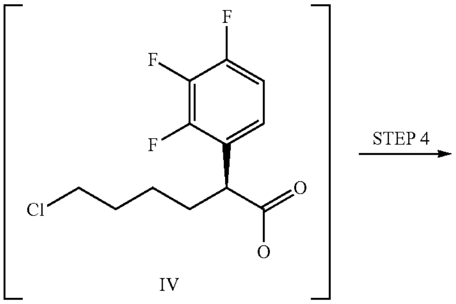

IV

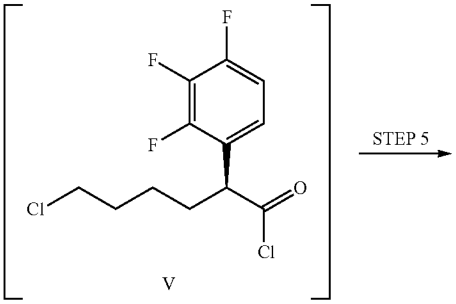

V

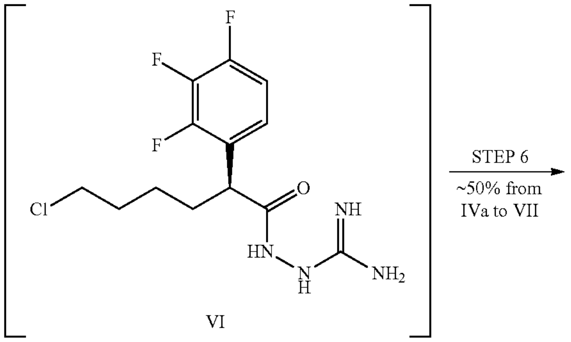

VI

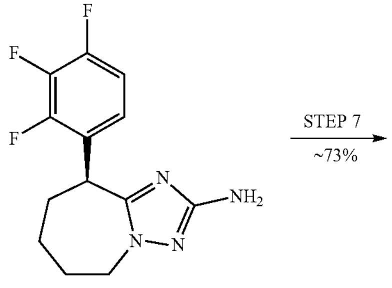

VII

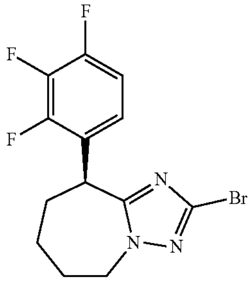

I

The synthesis comprises the following steps:

step 1) compound (III) formation, (III)

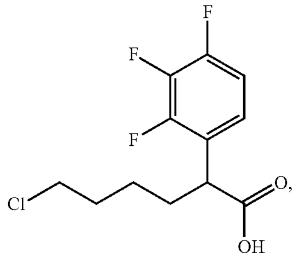

via the reaction of 2,3,4-trifluorophenylacetic acid, compound (II), (II)

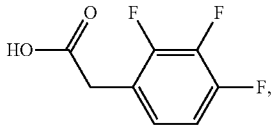

and 1-cloro-4-iodobutane;

step 2) compound (IVa) formation, (IVa)

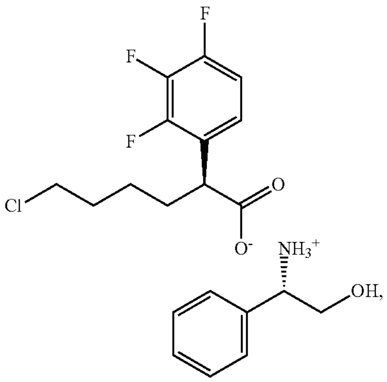

via chiral resolution of salt formation between a chiral base and compound (III);

step 3) the formation of (2S)-6-chloro-2-(2,3,4-trifluorophenyl)hexanoic acid, compound (IV), (IV)

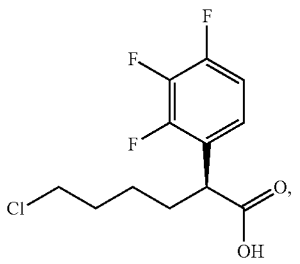

via dissociation of the compound (IVa) with acid;

step 4) the formation of (2S)-6-chloro-2-(2,3,4-trifluorophenyl)hexanoyl chloride, compound (V), (V)

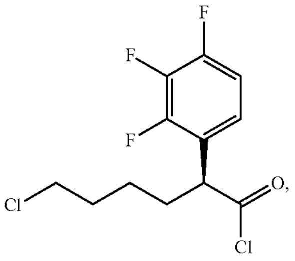

via acyl chlorination of compound (IV) with chlorinating reagent;

step 5) the formation of compound (VI), (VI)

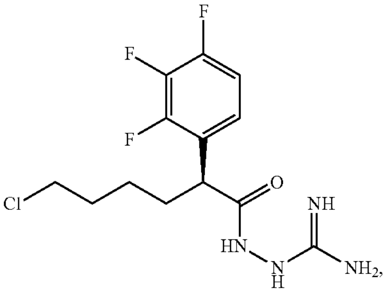

via coupling reaction between amino-guanidine and the compound (V);

Step 6) compound (VII) formation, (VII)

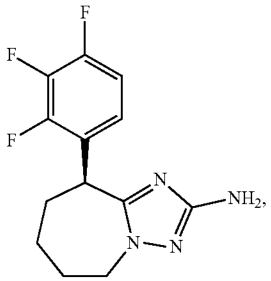

via intramolecular cyclization of compound (VI) in the presence of a base;

Step 7) compound (I) formation, (I)

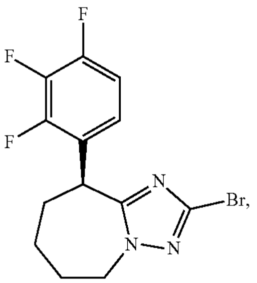

via the Sandmeyer reaction.

A detailed description of present invention of process steps is as following:

step 1) the compound (III) formation, (III)

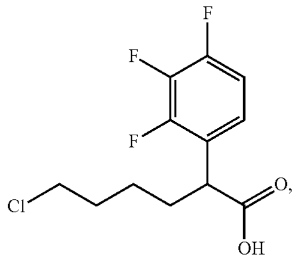

via the reaction of 2,3,4-trifluorophenylacetic acid, compound (II), (II)

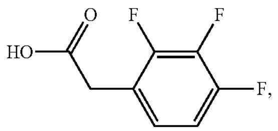

and 1-cloro-4-iodobutane and a base.

Compound (III) (288 kg, 89% purity, >90% yield) was synthesized in the presence of a suitable solvent, temperature with a suitable base.

The suitable solvent is selected from THF, n-Heptane, MeCN and MeTHF; particularly the solvent is THF.

The suitable temperature is selected from −5 to 5° C. and the suitable reaction time is from 1-3 hours, particularly the temperature is at 0° C. and the reaction time is 2 h.

The suitable base is selected from NaHMDS, KOtBu and LiHMDS, particularly the suitable base is NaHMDS.

In another embodiment, the reactants loading sequence were changed for the reaction, which was critical for the whole process in terms of technical scale manufacture and yield improvement. Adding NaHMDS to the solution of compound (II) in THF and 1-chloro-4-iodobutane at 0° C. for 3 h under agitating condition could achieve the best conversion result by IPC. Better and convenience work-up process were also developed by replacing HCl solution with citric acid solution and adjusting pH to 5-7 followed by extracting the mixture with IPAc to afford high quality product (III) solution for next step large scale (IVa) manufacture without column purification.

According to the published condition (WO2011086098), methyl ester of compound (III) was used for the tri-azole formation, which unfortunately gave a very low yield (~15.8%).

The crude product was used directly in the next step without solid isolation.

step 2) compound (IVa) formation, (IVa)

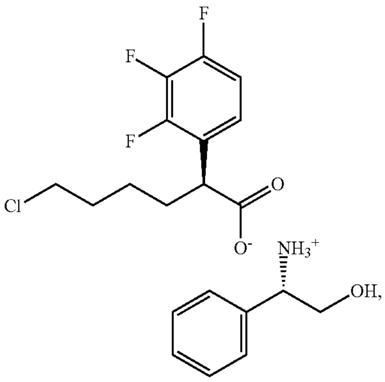

via chiral resolution of salt formation between a chiral base and compound (III) in a suitable solvent, compound (IVa) (164 kg, chiral purity 99.4%, 44% yield) was isolated.

The suitable chiral base is selected from quinidine, (R)-(+)-N-benzyl-α-methylbenzylamine, (S)-(+)-2-minobutanol, (S)-(−)-α-methylbenzylamine, Hydroquinine, (R)-(+)-2-amino-3-phenol-1-propanol, (1R,2R)-(+)-pseudoephedrine, (S)-(−)-phenylpropylamine, (R)-(−)-2-amino-1-propanol, N-methyl-D-glucamine, (−)-cinchonidine, (S)-(+)-phenylglycinol, dehydroabietylamine, (1R,2S)-(+)-cis-1-Amino-2-indanol, (1R,2R)-(−)-1,2-diaminocyclohexane, (1R,2R)-(+)-1,2-diphenylethylenediamine; particularly the chiral base is (S)-(+)-phenylglycinol.

The suitable solvent is selected from IPAc, THF, MTBE and IPA, particularly the solvent is IPAc.

The reaction is performed at 45° C.-55° C. then cool to 5° C.-15° C., particularly at 50° C. then cool to 10.4° C.

step 3) the formation of (2S)-6-chloro-2-(2,3,4-trifluorophenyl) hexanoic acid, compound (IV), (IV)

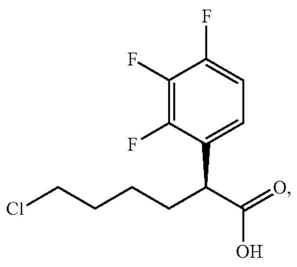

via dissociation of the compound (IVa) with aqueous HCl solution.

step 4) the formation of (2S)-6-chloro-2-(2,3,4-trifluorophenyl)hexanoyl chloride, compound (V), (V)

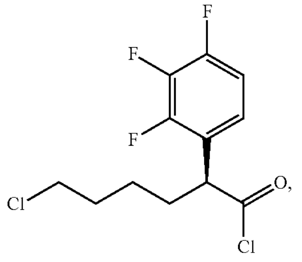

via acyl chlorination of compound (IV) with chlorinating reagent.

The suitable chlorinating reagent is selected from $(COCl)_2$ and $SOCl_2$, particularly the chlorinating reagent is $SOCl_2$.

The eq. of $SOCl_2$ was selected from 2.5 eq. to 5 eq., particularly the eq. is 5 eq.

The suitable solvent is selected from NMP and DCM/DMF, particularly the solvent is NMP.

The reaction is performed at 5° C.-20° C., particularly at 5° C.-15° C.

To address low yield concern of the amino tri-azole compound (VII) formation, the new formed (2S)-6-chloro-2-(2,3,4-trifluorophenyl) hexanoyl chloride, compound (V), was used for the desired amino tri-azole compound (VII) production instead of the methyl ester of (III). The new developed condition is a confirmed scalable process.

step 5) the formation of compound (VI), (VI)

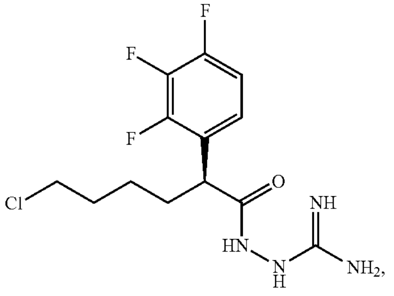

via coupling reaction between amino-guanidine and the compound (V).

The suitable solvent used in this step is selected from NMP, DCM, pyridine, dioxane and MeTHF; particularly the solvent is NMP.

The reaction is performed at 5° C.-125° C., particularly at 5° C.-15° C.

The reaction is performed from 1 to 20 hours, particularly the reaction time is 3 h.

Regioisomer, compound (VI-1), is also observed during the coupling of the acyl chloride and the amino guanidine, which was also considered in the development process. Compound (VI-1) and another major by-product, compound (VI-2), could be removed from developed recrystallization process.

VI-1

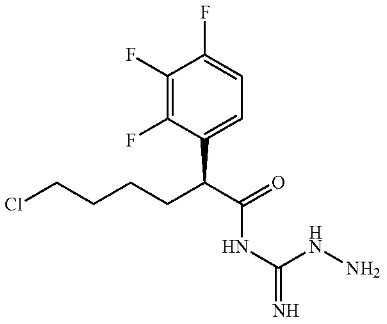

VI-2

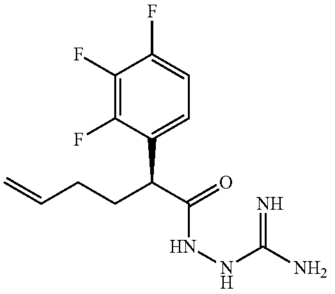

Step 6) compound (VII) formation, (VII)

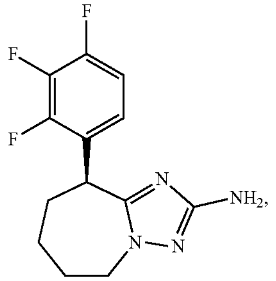

via intramolecular cyclization of compound (VI) in the presence of a base.

The suitable base is selected from NaOH, $NaHCO_3$, $Et_3N$, DIEA, $Na_2CO_3$, $K_2CO_3$, DBU and $K_3PO_4$, $K_3PO_4$/KI; particularly the base is $K_3PO_4$/KI. The developed condition is very important to avoid the racemization in this step, especially the base selection is critical. Strong base, NaOH can cause over 30% racemization in this step.

The suitable solvent is selected from DMF, MeCN, MeTHF, IPA and NMP; particularly the solvent is IPA. The correct solvent selection is also critical to the reaction and crystallization to achieve high yield.

The reaction is performed at 60° C.-105° C., particularly at 75° C.-85° C.

The reaction time is performed from 5 to 18 hours, particularly the reaction time is 16 h.

Step 7) compound (I) formation, (I)

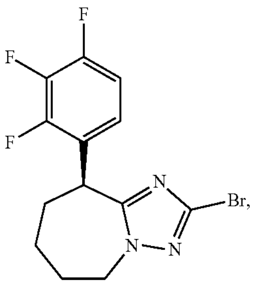

via the Sandmeyer reaction in the presence of nitrate reagent and a catalyst in a suitable solvent. The recrystallization was performed to achieve 99.9% purity, 100.0% chiral purity in 70% yield.

The suitable nitrate reagent and catalyst are selected from $NaNO_2$/HBr and t-BuONO/$CuBr_2$; particularly the reagent and catalyst are t-BuONO/$CuBr_2$. The suitable equivalent of t-BuONO/$CuBr_2$ is 1.7 eq to 1.3 eq; particularly the equivalent is 1.5 eq. The selection of nitrate reagent and catalyst as well as their equivalent was critical to achieve the highest yield and the minimum by-products, compound (I-1) and compound (I-2).

| Test No. | Amount of compound (VII) | Reaction condition | Compound (I-2) | Compound (I-1) | HPLC purity |
|---|---|---|---|---|---|
| 1 | 2 g | 1.7 eq. of t-BuONO and $CuBr_2$; MeCN (6 v) at ~60° C. for 1 h | 3.6% | <0.5% | 81.7% |
| 2 | 20 g | 1.5 eq. of t-BuONO and $CuBr_2$; MeCN (6 v) at ~45° C. for 1 h | 2.0% | <0.5% | 81.0% |
| 3 | 10 g | 1.4 eq. of t-BuONO and $CuBr_2$; MeCN (5v) at ~45° C. for 3 h | 2.3% | <0.5% | 80.3% |
| 4 | 17 g | 1.3 eq. of t-BuONO and $CuBr_2$; MeCN(15 v) at ~60° C. for 1 h | 1.0% | ~24% | 54% |

The suitable solvent is selected from MeCN, MeTHF, THF, IPA and NMP; particularly the solvent is MeCN.

Reaction volume for MeCN was tried to decrease from 15 to 5 volume and all reactions can give full conversion; particularly the solvent volume is 6 volume.

The reaction time is 1.5-22 hrs, the reaction is performed at 25-60° C., particularly the reaction is performed at 45° C. for 3 hours.

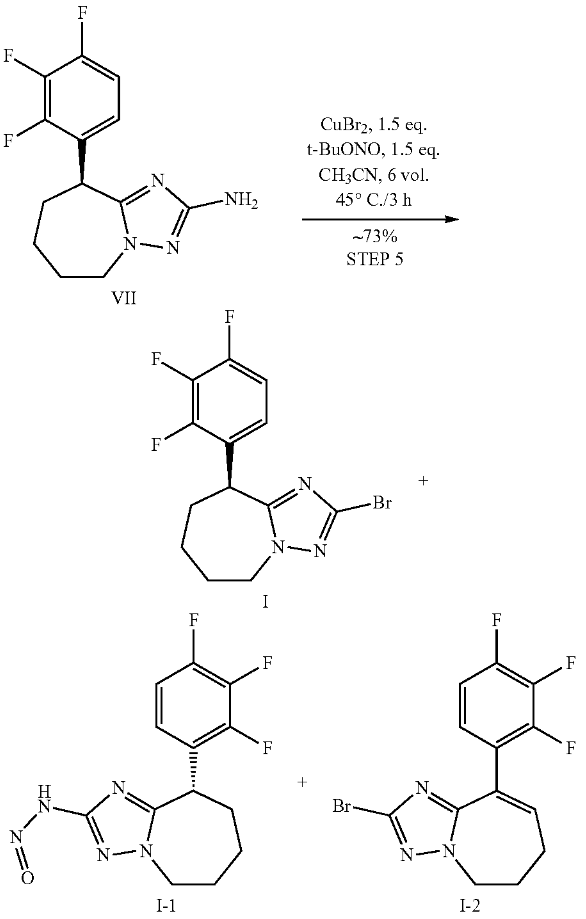

VII

I

+

I-1

+

I-2

(Compound (I-1) and (I-2) were observed in HPLC and the structures were drawn tentatively.)

EXAMPLES

The invention will be more fully understood by reference to the following examples. They should not, however, be construed as limiting the scope of the invention.

Example 1

6-chloro-2-(2,3,4-trifluorophenyl) hexanoic acid (Compound (III))

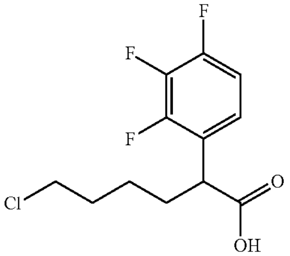

To a 3000 L glass-lined (GL/3000 L) Pilot Plant reactor under $N_2$ protection was charged with 2,3,4-trifluorophenylacetic acid (compound (II), 102.3 kg, 1.0 eq.), THF (590 kg)

at 15° C.-25° C. After being stirred for 30 min, the reaction mixture was charged with 1-chloro-4-iodobutane (130 kg, 1.9 eq.), then the reactor inner temperature was adjusted to −5~5° C. under nitrogen protection. NaHMDS (1M/THF, 956 kg, 2.0 eq.) was added slowly into the reactor for at least 1 h at −5~5° C. under nitrogen protection, the reaction mixture was stirred at −5~5° C. for 1~3 h.

Water (200 kg) was charged slowly in portions via vacuum to the reaction mixture to the reactor above with batch temperature at −5~5° C. under nitrogen protection. Then the temperature was adjusted to 15~25° C. under nitrogen protection, and 38% citric acid aqueous solution (372 kg) was charged in portions via vacuum till pH was 7 at 15~25° C. and the reaction mixture stood for 0.5~1.5 h.

The aqueous layer was removed and IPAC (309 kg) was charged via charging device and diaphragm pump The separated organic mixture was concentrated at (<30° C. inner temperature) under reduced pressure to ~206~515 L to remove THF. Then IPAc (422 kg), 25% NaCl aqueous solution (180 kg) and process water (122 kg) were charged into the resulting residual via charging device and diaphragm pump at 20-30° C. The mixture was stirred for 1 h and then the aqueous layer was separated.

Two organic layers were combined (~1000 L) and concentrated. The residual was azeotroped with IPAc (2×450 L) to remove water to required limitation by IPC to get product of compound (III) (net 288 kg) in IPAc solution for next step use without any further treatment.

The crude [1]NMR: $^1H$ NMR (300 MHz, CDCl3) δ=7.08-6.96 (m, 2H), 3.98 (t, J=7.2 Hz, 1H), 3.51 (t, J=6.2 Hz, 2H), 2.17-2.09 (m, 1H), 1.87-1.75 (m, 3H), 1.51-1.37 (m, 2H), 0.18 (s, 18H).

Example 2

Synthesis of (2S)-6-chloro-2-(2,3,4-trifluorophenyl) hexanoate;[(1S)-2-hydroxy-1-phenyl-ethyl]ammonium (Compound (IVa)) and Compound (IV)

(IVa)

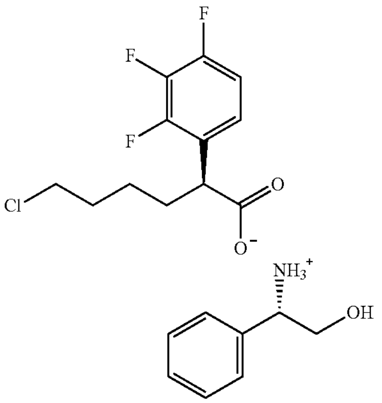

(IV)

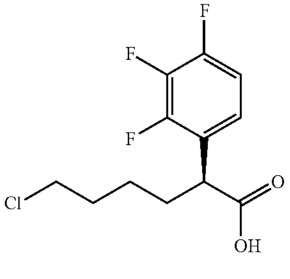

To an 8000 L glass-lined reactor was charged compound (III) in isopropyl acetate (167 kg) and IPAC (4004 kg) via diaphragm pump, the mixture was heated to 50° C. and stirred till clear. L-phenylglycinol (27 kg) and IPAc (155 kg) were charged into the clear solution and the mixture was stirred at 45-55° C. for 2.5 h. Crystal seed (0.08 kg) was added to the mixture which was stirred at 50° C. for another 2.5 h. Another part of L-phenylglycinol (55.8 kg) and IPAc (155 kg) were charged into the mixture which was stirred at 50° C. for another 8 h, and then cooled to 10° C. with further stirring for 15 h to result a suspension. The suspension was filtered and the filter cake was washed in the centrifuge with cold IPAc (380+187 kg, 10° C.) to afford crude compound (Iva) (228 kg, 96% ee).

Recrystallization

The crude IVa (228 kg) and IPAc (2958 kg) were charged into the 8000 L reactor. The mixture was heated to 50° C. with stirring for 8 h, then cooled to 10° C. and stirred for 15 h to result a suspension. The suspension was filtered and washed with cold IPAc (381+191 kg) at 10° C. to get a pure compound (Iva) (164 kg, 99.4% ee) as a wet cake, which was used for next step without other operation.

Free Acid Compound (IV) Preparation

35% HCl (106 kg), process water (502 kg) and DCM (1477 L) were charged under $N_2$ to the 8000 L reactor. The mixture was stirred for 30 min. The wet cake of compound (IVa) (164 kg) and process water (338 kg) were added at 10° C. to the solution and the mixture was stirred for another 1 h, then 2M HCl (381 kg) was added to adjust pH=2 at 10° C. The temperature was then adjusted to 25° C. and the mixture was stirred for 3 h to afford a diphase clear solution. The solution was settled for 1.5 h and separated. The lower layer (organic phase) was washed with NaCl solution (10.1 kg NaCl in 328 kg water) which was extracted with DCM (207 L) and the top layer (inorganic) was extracted with two times DCM (107 kg and 106 kg). The combined DCM layer was concentrated under vacuum (<40° C.) and was azeotroped two times with DCM (513 L and 514 L) to remove water to result compound (IV) in DCM solution (net weight 1426.6 kg, IPC water content ~0.04%, with 72.2 kg compound (IV)), 44% yield for these two steps. 99.2% ee, 96% chemical purity for compound (IV), which was used directly for next step without further operation.

Example 3

Preparation of Compound (V), (VI) and (VII) from Compound IV

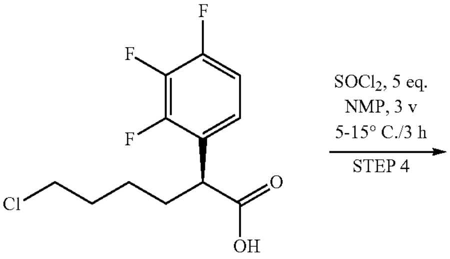

IV

-continued

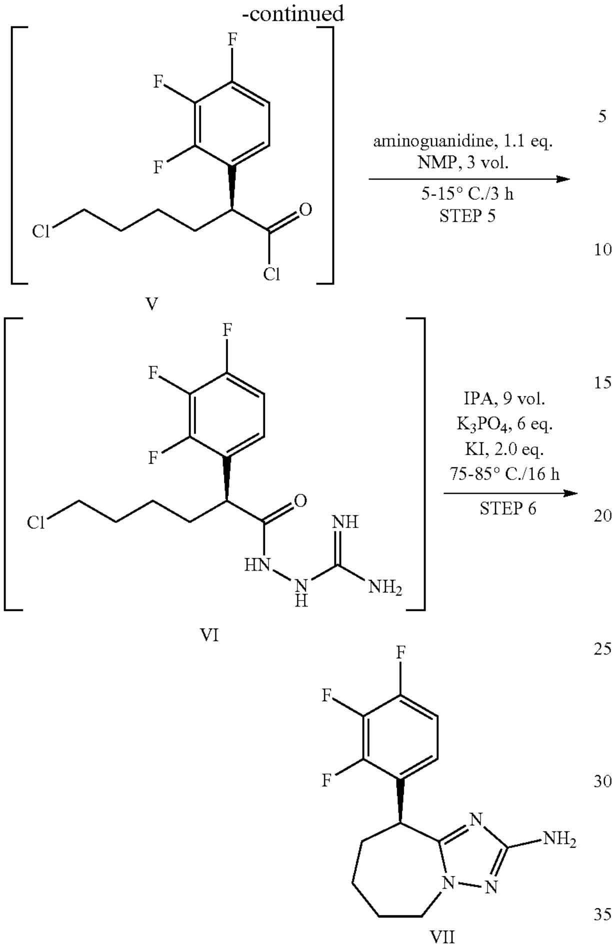

V

VI

VII

Production of compound (VII) from 72.2 kg of compound (IV) in one batch was finalized in plant according to the following procedure. Finally, 38.20 kg of compound (VII) was obtained with 99.3% purity, 97.5% chiral purity and 95.8% assay in 50% yield.

The DCM solution (1426 kg in total) of compound (IV) (72.2 kg) from previous step in 1000 L reactor was concentrated to 71-142 L, then NMP (225 kg) and thionyl chloride (34.8 kg, 2.5 eq.) was charged with stirring at 5~15° C. under nitrogen protection. The reaction mixture was stirred for 3 h and was charged aminoguanidine hydrochloride (31.2 kg, 1.1 eq.) at 5~15° C. under nitrogen protection to form compound (VI) after the mixture was stirred for another 3 h. Process water (352+104 kg) was added at 5~15° C. in portions to the mixture followed by adding IPAc (622+225 kg) at 5-15° C. Then 30% $K_3PO_4$ solution (726+50 kg) was added slowly to the mixture under 20° C. till pH=8.1 followed by adding process water (70 kg) dropwise into the mixture via peristaltic pump. After stirring the mixture at 20° C. for 60 min., the aqueous layer was separated and extracted with IPAc (282 kg). The combined organic layer was concentrated (<45° C.) till 71-282 L left and azeotroped the residual (<45° C.) with IPA two times (446+639 L) to get 71-497 L solution (with IPAc content ~0.01). To the residue solution, IPA (535 L), KI (85 kg) and $K_3PO_4$ (300 kg) were charged via flexible isolator under nitrogen protection followed by adding process water (470 kg) to the mixture at 10-30° C. The mixture was stirred at 75-85° C. for 20 h and then cooled to 45-60° C. before the aqueous layer was separated. The organic layer was further cooled to 35-45° C. and then was charged compound (VII) crystal seed (0.055 kg) with stirring for another 2 h. The mixture was cooled to 0-10° C. over 1 h followed by adding process water (289 kg) at 0-10° C. under $N_2$ with stirring for 12 h to achieve a suspension. The suspension was filtered with centrifuge and the filter cake was washed with IPA/water (ratio 31/36, 36 kg) and process water two times (350+58 kg) under $N_2$ to afford compound (VII) (41.25 kg, purity 99.4, chiral purity 97.5%). The wet cake was dried under reduced pressure at 55° C. for 30 h to achieve solid compound (VII) (38.2 kg). Impurities of compound (VI-1) and (VI-2) were removed during the recrystallization.

Compound VII: $^1H$ NMR (300 MHz, DMSO-$d_6$) δ=7.032-7.17 (m, 2H), 6.23 (s, 2H), 4.34 (m, 1H), 4.15-3.99 (m, 2H), 2.14-1.93 (m, 4H), 1.92-1.76 (m, 1H), 1.60-1.48 (m, 1H).

Examples 4

Preparation of Compound (I)

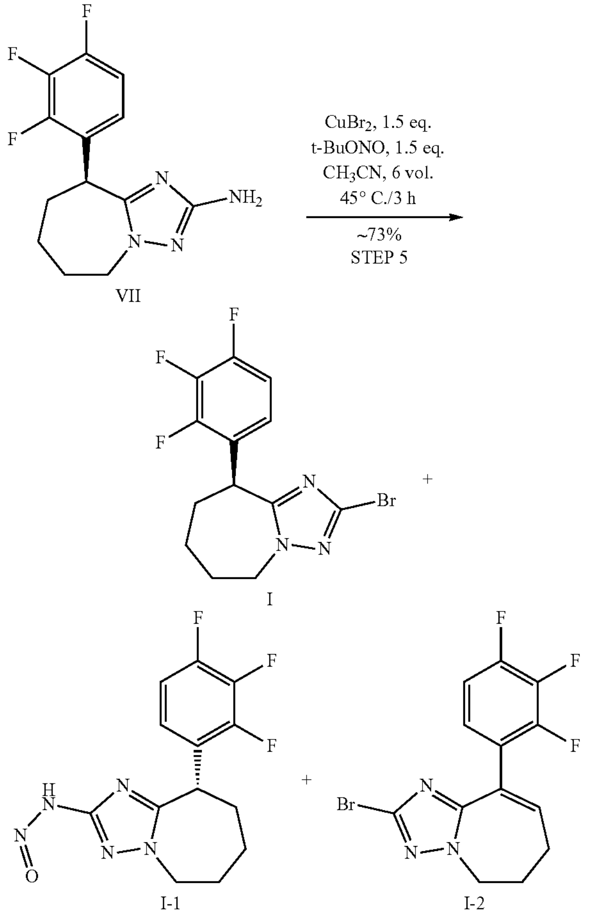

VII

I

I-1

I-2

(Compound (I-1) and (I-2) were observed in HPLC and the structures were drawn tentatively.)

Production of compound (I) from 36.50 kg of compound (VII) in one batch was finalized in plant according to following procedure. Finally, 31.10 kg of compound (I) was obtained with 99.9% purity, 100.0% chiral purity and 96.3% assay in 73% yield.

The solid of compound (VII) (35 kg), MeCN (141 kg+29 kg) and $CuBr_2$ (41.6 kg) were charged into 1000 L GL reactor via flexible isolator under $N_2$ protection. The mixture was heated to 40~50° C. followed by slowly adding tert-Butyl nitrite (19.2 kg) and MeCN (7 kg) in portions under $N_2$ protection. The mixture was stirred at 40~50° C. for 5 h, cooled to 15~25° C. and then added IPAc (472 kg), process water (176 kg). The mixture was stirred for 10 h and was filtered through diatomite (10 kg). After rinsing the filter cake with IPAc (101 kg), the aqueous layer was separated. And then the organic layer was concentrated under vacuum to 140-210 L. The residual solution is azeotroped four times with MeOH (140, 125, 123, 126 kg) to achieve a 140~210 L solution with desired quality (IPAc~28938 ppm). The mixture was heated to 60~70° C. to get a clear solution and stirred for 2 h. The solution was cooled to 5~15° C. with stirring under $N_2$ for 24 h to result a suspension. The suspension was filtered and the wet cake was rinsed with MeOH (16 kg) to obtain a solid cake of compound (I) (36.2 kg, 99.8% ee, 97.4% purity).

Recrystallization

EA (514 kg) was charged to the solid cake of the crude compound (I) in the 1000 L reactor and the mixture was stirred at 30~40° C. to get a solution. The mixture was concentrated at <35° C. to 280~350 L and then cooled to 20~30° C. of batch temperature under $N_2$ protection. Compound (I) crystal seed (0.058 kg) was charged into the reactor at 20~30° C. and the solution was stirred for 2 h. The solution is azeotroped three times with MeOH (114, 108, 106 kg) to achieve a 105~175 L final solution to remove EA with desired IPC (EA~3967 ppm). The MeOH solution (105~175 L) of the crude compound (I) was stirred at 40~50° C. for 2 h and cooled to 5~15° C. with stirring for another 20 h to afford a suspension, which was filtered. The wet cake was rinsed with MeOH (17 kg) and dried under vacuum at 35° C. for 15 h to obtain pure compound (I) (31.1 kg, 99.9% ee, 99.6% purity) as a white solid. Impurities of compound (I-1) and (I-2) were removed during the recrystallization.

Compound (I): $^1H$ NMR (400 MHz, DMSO-$d_6$) δ=7.38-7.28 (m, 1H), 7.27-7.17 (m, 1H), 4.55 (dd, J=3.4, 9.8 Hz, 1H), 4.50-4.39 (m, 1H), 4.38-4.23 (m, 1H), 2.14-1.93 (m, 4H), 1.92-1.78 (m, 1H), 1.70-1.51 (m, 1H)

The invention claimed is:

1. A process for the preparation of compound (I), (I)

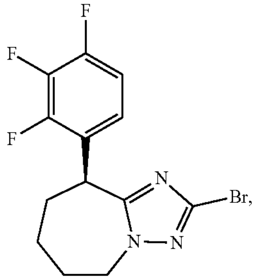

or a pharmaceutically acceptable salt thereof, the process comprising any of the following:

a) forming compound (III)

(III)

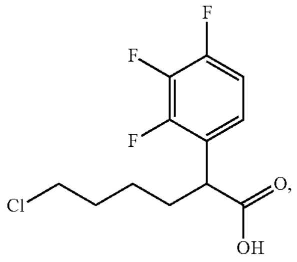

via reaction of 2,3,4-trifluorophenylacetic acid (II)

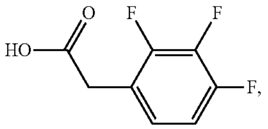

with 1-cloro-4-iodobutane;

b) forming compound (IVa)

(IVa)

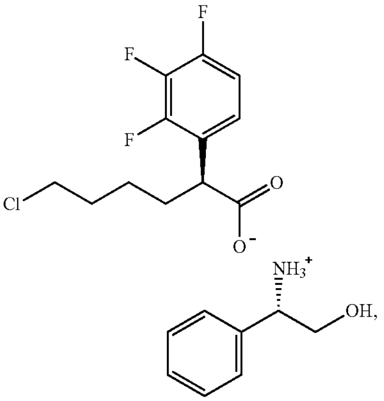

via chiral resolution of salt formation between (S)-(+)-phenylglycinol and compound (III)

(III)

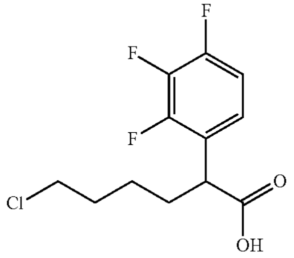 [SMILES: O=C(O)C(CCCCCl)c1ccc(F)c(F)c1F]

in the presence of IPAc;

c) forming (2S)-6-chloro-2-(2,3,4-trifluorophenyl) hexanoic acid, compound (IV), (IV)

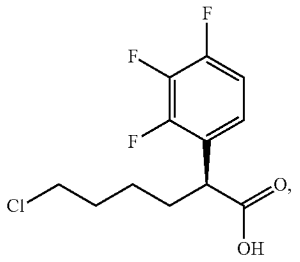

via dissociation of compound (IVa) with acid;

d) forming (2S)-6-chloro-2-(2,3,4-trifluorophenyl) hexanoyl chloride, compound (V), (V)

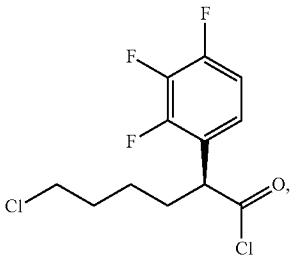

via acyl chlorination of compound (IV) with a chlorinating reagent;

e) forming compound (VI)

(VI)

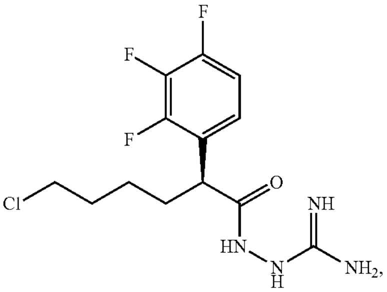

via coupling reaction between amino-guanidine and compound (V);

f) forming compound (VII)

(VII)

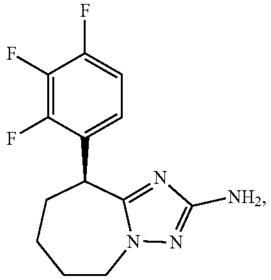

via intramolecular cyclization of compound (VI) in the presence of $K_3PO_4$/KI in IPA; and g) forming compound (I)

(I)

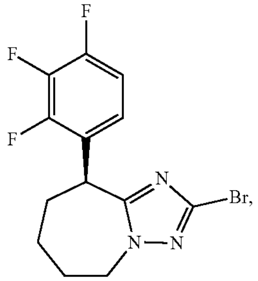

via a Sandmeyer reaction in the presence of 1.5 eq t-BuONO/$CuBr_2$.

2. A compound having the structure of compound (IVa)

(IVa)

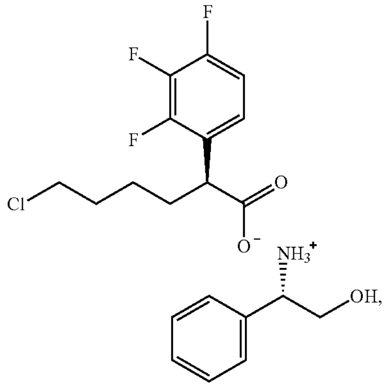

or (2S)-6-chloro-2-(2,3,4-trifluorophenyl)hexanoate:[(1S)-2-hydroxy-1-phenyl-ethyl] ammonium.

* * * * *